United States Patent [19]
Lichenstein

[11] Patent Number: 5,516,685
[45] Date of Patent: May 14, 1996

[54] ISOLATION AND CHARACTERIZATION OF A NOVEL PROTEASE FROM *STREPTOMYCES LIVIDANS*

[75] Inventor: Henri Lichenstein, Ventura, Calif.

[73] Assignee: Amgen Inc., Thousand Oaks, Calif.

[21] Appl. No.: 272,882

[22] Filed: Jul. 7, 1994

Related U.S. Application Data

[63] Continuation of Ser. No. 724,721, Jul. 1, 1991, abandoned.

[51] Int. Cl.$^6$ .............................. C12N 1/21; C12N 9/52; C07H 21/04
[52] U.S. Cl. .................... 435/252.35; 536/23.2; 536/23.1; 435/320.1; 435/172.3; 435/212; 435/219; 435/69.1; 435/252.3; 935/14
[58] Field of Search .................. 435/320.1, 172.3, 435/69.1, 220, 194, 252.35, 866, 195, 212, 219, 252.3; 536/23.2, 23.1, 24.32; 935/14, 10, 11

[56] References Cited

U.S. PATENT DOCUMENTS 4,865,982 9/1989 Burnett, Jr. et al. ............... 435/252.35

FOREIGN PATENT DOCUMENTS

WO89/10976 11/1989 WIPO.

OTHER PUBLICATIONS

Watson, J. D. 1987. in: *Molecular Biology of the Gene*. 3rd Edition. Benjamin/Cummings Publ. Co., Menlo Park, CA p. 313.

Gibb etal. 1986. Abstr. Ann. Meeting/Am. Soc. For Microbiol. p. 211 abstract K105.

Lichenstein et al. (1988) J. Bacteriology 170(9):3924–3929.

Lichenstein et al. (1992) Gene 111: 125–130.

Duez et al. (1990, Sep. 1 ) FEMS Micro. Lett. 71:215–220.

Henderson et al. (1987) J. Bacteriology 169(8):3778–3784.

Noack et al. (1988) Gene 68:53–62.

Tomich et al. (1988) Antimicrob. Agents Chemo. 32(10):1465–1471.

Woodcock et al. (1989, Feb.) Biochem. Soc. Trans. 17(1):183.

Aretz et al. (1989, Nov.) FEMS Micro. Lett. 65:31–35.

*Primary Examiner*—Christopher S. F. Low

[57] ABSTRACT

The isolation and characterization of a novel polypeptide, designated Protease X, identified while screening for proteases exported into the media by *Streptomyces lividans*, is described [SEQ ID NO: 2]. Also disclosed is the DNA sequence of the gene encoding this protein [SEQ ID NO: 1]. The polypeptide was found to have proteolytic activity on the substrate succinyl-ala-ala-pro-phe-pNitroanilide, also cleaved by chymotrypsin, subtilisin, and cathepsin G. In addition, methods for purifying the protease and raising antibodies against it are reported. Lastly, the generation of an *S. lividans* strain deficient in this proteolytic activity is reported. Such a strain may prove useful as a host for production of heterologous protein products.

6 Claims, 2 Drawing Sheets

FIG. 1A

```
aagcttctagaGATCCCGCCCCCTTCCAGCCACTCCCGGTACGCGGTGGACTGGCGGGCG    60
GCCTCCCAGTACGCGTCCTCCAGGGCGGGGAAGACCGCGTCCAGCTCGGCCCGGGTGCGG   120
GCGGCCAGCAGCAGGCGTACGCCGAGGGGGTCGCCGTACAGGCGCCGCACCGCCGTGTCG   180
GGGCGGGACTGGGAACTGGGCTGGCAGACCGTGACGACCTCGCCGGTGGCGACCAGGGAG   240
GCGGCCGTGTGGTAGTCGCCGTGCAGCACCCGGGGGTTGAGGCCGACGGCGCGCAGCATG   300
                                                          M
CGGTGCACGCCGTCCCATTCGCCGTCGACGGTGGGGTCGACCATCCACCGGTCGTCGGCG   360
 R  C  T  P  S  H  S  P  S  T  V  G  S  T  I  H  R  S  S  A
AGGTCGGCGAGGCGGACGACGGGCCGGGCGGCCGCGGGGTGGTCGGCGGGCAGCATGACG   420
 R  S  A  R  R  T  T  G  R  A  A  A  G  W  S  A  G  S  M  T
AACTGCGGTTCGCGCTCGACCAGGACGCGCAGCCGCAGGTCCTCGGGGATGTGCAGCGCA   480
 N  C  G  S  R  T  R  T  R  S  R  R  S  S  G  M  C  S  A
CAGCCCTCGACCTCGTGCACGAAGGCGACGTCGAGCTGACCGTCGGTCACCCGGCGCAGC   540
 Q  P  S  T  S  C  T  K  A  T  S  S  *
AGCGCGTTGGCGGAGACGTCCATCTGCAGGGTCGGTTCCAGGCCCGGCCGTCTGAGCCGG   600
CGCAGCCAGCCGGCCAGGGCCCGGCTGGCCGTGGAGCCGACCCGCAGCCTGCTGTCGCCG   660
CCGGCCGCGGCGGCGCGGGCCTCGCGGACCAGGGTGTTCATGTCGGTCAGCAGCGGACGG   720
                                    M  S  V  S  S  G  R
GCCCGGCCGAGCACCGTCCGGCCGAGCGGGGTGGGCGGCAGCCGGTGCGCTCCCGGGTG   780
 A  R  P  S  T  V  R  P  S  G  V  G  R  Q  P  V  R  S  R  V
AACAGCGGTCCGCCCAGGGCCTGTTCGATGCGGGTCAACTGAGTGCTCAACGTGGGCTGT   840
 N  S  G  P  P  R  A  C  S  M  R  V  N  *
GCGACACCCAGTCGGCGTGCCGCCCGGTGCAGGCTGCCGGCGTCGGCGATGGCGCACAGT   900
GCGCGTAGGTGCCTCACCTCGAGCTCCATGCAGGGAGCGTAAAGCGGAACAGTTGGTTGC   960
GCCAGGTGAACAAAACGCGGCGGATCAGGGCGAGTTCTGCACTCTGGTCAAAGCTGGAAC  1020
GAGAGTGGCCGGGCGGTGGGTGATAGCCCGGCCCTATCACCTGTTGCCATCATCACAGCG  1080
GGCTCATGGGCGCCCCACACTCACCGGTGACGACTTCTCCCCACTCCCCACTCAAGGAG  1140
```

FIG.1B

```
TCATCGATGCGTATCACCCTGCCCCTTCTTTCCACCGCGGTCGGTCTCGGCCTGACGGCC  1200
      M  R  I  T  L  P  L  L  S  T  A  V  G  L  G  L  T  A

GCCGTGCTCGGCACCGGCCCCGCCGCGACGGCCGCGGCGCCCCAGGAGCCGGTCAGAGCC  1260
 A  V  L  G  T  G  P  A  A  T  A  A  A  P  Q  E  P  V  R  A

GCCCAGCTCGGCTACCAGCCCTCGGCCGGCTCGGGCGAGGACGCGGCCGCCAACCGCGCG  1320
 A  Q  L  G  Y  Q  P  S  A  G  S  G  E  D  A  A  A  N  R  A

TTCTTCGAGGCGGTCGTCAAGTCCGTCGCCGAGAAGCGCGCCGCCAACCCGTCCGCCGCC  1380
 F  F  E  A  V  V  K  S  V  A  E  K  R  A  A  N  P  S  A  A

GCGGCCGTCACCGTCTACTACAGCGCCACCAACGCGCCGAGCTTCCGTTCCCAGATATCC  1440
 A  A  V  T  V  Y  Y  S  A  T  N  A  P  S  F  R  S  Q  I  S

CGCTCCGCCCAGATCTGGAACAGCTCGGTGTCCAACGTACGGCTCGCGGAGTCGAGTTCC  1500
 R  S  A  Q  I  W  N  S  S  V  S  N  V  R  L  A  E  S  S  S

GGCGCGGACTTCGCGTACTACGAGGGCAACGACTCGCGCGGCTCGTACGCGTCCACGGAC  1560
 G  A  D  F  A  Y  Y  E  G  N  D  S  R  G  S  Y  A  S  T  D

GGGCACGGCAGCGGCTACATCTTCCTCGACTACCGCCAGAACCAGCAGTACGACTCGACC  1620
 G  H  G  S  G  Y  I  F  L  D  Y  R  Q  N  Q  Q  Y  D  S  T

CGCGTGACCGCCCACGAGACCGGGCACGTGCTCGGCCTGCCCGACCACTACTCCGGGCCG  1680
 R  V  T  A  H  E  T  G  H  V  L  G  L  P  D  H  Y  S  G  P

TGCAGCGAGCTGATGTCGGGCGGCGGCCCCGGCCCGTCCTGCACCAACCCCTACCCGAAC  1740
 C  S  E  L  M  S  G  G  G  P  G  P  S  C  T  N  P  Y  P  N

TCCACCGAGCGCAGCCGGGTGAACCAGCTGTGGGCCTACGGCTTCCAGGCCGCCCTCGAC  1800
 S  T  E  R  S  R  V  N  Q  L  W  A  Y  G  F  Q  A  A  L  D

AAGGCGCTGGAGAAGGCCTCCCAGCGCTGACGTACGCGGACCACCGTGCGGGCGGCCCGG  1860
 K  A  L  E  K  A  S  Q  R  *

CCGGGCCGCCCGCACGCGTGCGCGCTCCCTCCACCTCCGCTTGGGCAACC             1910
```

ISOLATION AND CHARACTERIZATION OF A NOVEL PROTEASE FROM *STREPTOMYCES LIVIDANS*

This application is a continuation of application Ser. No. 07/724,721, filed Jul. 1, 1991 now abandoned, which is hereby incorporated by reference.

FIELD OF THE INVENTION

The present invention relates to the isolation and characterization of a novel protease. Specifically, the present invention describes the isolation and characterization of a previously unidentified protease secreted from *Streptomyces lividans* [SEQ ID NO: 2]. In addition, the DNA sequence encoding the protease is also described [SEQ ID NO: 1].

BACKGROUND OF THE INVENTION

Streptomyces species are attractive hosts for the secretion of heterologous proteins because they are non-pathogenic, efficiently secrete proteins directly into the media, and their cultivation on an industrial scale is well understood. Currently, *S. lividans* is being utilized as the prototype host for the export of heterologous proteins from Streptomyces since detailed procedures have been established for its manipulation via classical genetic or recombinant DNA technologies [*Genetic Manipulations of Streptomyces*, Hopwood et al., Eds., The John Innes Foundation, 1985]. Indeed, *S. lividans* has been used as a host to direct the export of human interleukin 1β, *E. coli* β-galactosidase, *E. coli* alkaline phosphatase, human tumor necrosis factor, and human interferon α-1 [Bender et al., (1990) *Gene*, vol. 86, pp: 227–232; Lichenstein et al., (1988) *J. Bact.*, vol 170, pp: 3924–3929; Noack et al., (1988) *Gene*, vol. 68, pp: 53–62; Chang et al. in T. Okami et al., (1988) *Biology of Actinomycetes*, Japan Soc. Press, Tokyo, pp: 103–107].

Of particular concern in the use of *S. lividans* as a host for the secretion of heterologous proteins is degradation of the exported products by endogenous proteolytic activities. Numerous proteases have been shown to be secreted by *S. lividans* and these proteases could potentially damage the desired product [Aretz et al., (1989) *FEMS Microbiology Letters*, vol. 65, pp: 31–36]. To date, there have been no reports describing the cloning of a protease gene from *S. lividans*. The isolation of such a gene could prove invaluable in that the gene encoding the protease could be modified using recombinant DNA techniques to eliminate the proteolytic activity of the protein. The mutated gene for this deactivated protease would then be substituted for the wild-type protease gene by chromosomal integration. The resulting *S. lividans* strain would be protease-deficient and better suited for the secretion of heterologous protein products.

Isolation of a protease gene could also be useful in the design of vectors directing the expression and secretion of heterologous proteins from *S. lividans*. As proteins secreted from *S. lividans* are generally first synthesized with a leader peptide, it is likely that a secreted endogenous protease from *S. lividans* would contain such a leader or signal sequence. Thus, this leader peptide sequence could be used to direct the export of heterologous proteins. Additionally, regulatory sequences for the protease might also prove useful in enhancing the expression of the heterologous protein.

Use of an endogenous signal sequence to direct secretion of a foreign protein would facilitate the proper processing of the signal peptide by the *S. lividans* export machinery. Signal sequences isolated from other Streptomyces species, or isolated from other bacterial genera, may not function efficiently, or at all, in *S. lividans*. To date, the β-galactosidase signal peptide has been the only signal peptide isolated from *S. lividans* that has been used to direct the export of heterologous proteins from this organism [Lichenstein et al, (1988) supra].

The isolation of a novel protease gene from *S. lividans* may also define a protease with a unique activity which could prove commercially useful. For example, it is known that Streptomyces proteases, as well as those from other microbial species, are used in the food (protein liquefaction, milk clotting, meat tenderizing), pharmaceutical (fibrinolytic, thrombolytic), and tanning industries or as detergent additives. They can also be used in the research environment in the structural determination of proteins or in the removal of proteinaceous material during biopreparations. Examples of Streptomyces protease preparations that are commercially useful include PRONASE™ (*S. griseus*) and FRADIASE™ (*S. fradiae*). Other Streptomyces proteases have been isolated and together they comprise a large pool of proteases having various substrate specificities [Goodfellow et al. (Eds.), *Actinomycetes in Biotechnology*, 1988, Academic Press, pp: 246–250]. The cloning of such protease genes from *S. lividans* would allow the amplification of protease production such that sufficient quantities could be generated for any commercial application in which the protease could be utilized.

SUMMARY OF THE INVENTION

The present invention is directed to a novel protease [SEQ ID NO: 2] secreted into the culture medium by *S. lividans*. This protein is designated Protease X. One aspect of the present invention comprises the DNA sequence which codes for this protein [SEQ ID NO: 1]. Such sequences can be derived from natural sources, or, alternatively, they may be produced in whole or in part by synthetic means. DNA sequences which code for polypeptides having the biological activity of Protease X but which differ from the natural sequence are further envisioned by the present invention.

In another aspect, this invention envisions the introduction of DNA sequences encoding Protease X into recombinant vectors which, when transformed into suitable host strains, enable the production of a polypeptide product having the biological activity of Protease X. Also envisioned by the present invention are biologically active Protease X analogs having one or more deletions, insertions, and/or substitutions in or to the primary amino acid structure of the protein. Both procaryotic and eucaryotic microorganisms may serve as hosts for producing this novel proteolytic polypeptide. The procaryotic organisms *S. lividans*, *Bacillus subtilis*, and *Escherichia coli* will be particularly useful as hosts for the production of Protease X.

In yet another aspect, the present invention consists of antibodies which are specific in their ability to recognize and bind to polypeptides having at least some or all of the biological activity of Protease X.

Still another aspect of the instant invention involves the generation of DNA sequences encoding a polypeptide having an amino acid deletion sufficient to substantially eliminate the biological activity of the novel protease disclosed herein. In particular, a deletion of 0.3 kb from within the coding region of the protease is sufficient to substantially eliminate the protein's biological activity. Further, recombination of such deletion mutants with the wild-type gene located in the *S. lividans* chromosome results in a strain deficient in the biological activity attributed to Protease X. Such strains may be useful as hosts for recombinant expression of useful heterologous protein products.

In yet another aspect of the present invention, the DNA sequence encoding the signal peptide for Protease X will be useful in targeting heterologous proteins for export when such proteins are expressed in association with the leader peptide when expression occurs in procaryotic hosts, particularly *S. lividans*.

BRIEF DESCRIPTION OF THE FIGURES

FIG. 1 is the nucleotide sequence of the coding and flanking regions of Protease X from TK24 [SEQ ID NO: 1]. The first eleven nucleotides (in lower case letters) are derived from the polylinker site in pIJ699. ORF1 extends from nucleotide 298–516, ORF2 extends from nucleotide 700–819 and Protease X extends from nucleotide 1147–1827. Amino acids are aligned with the first letter of each codon and asterisks represent stop codons. Putative ribosomal binding sites are underlined, as is a putative transcriptional terminator in the 3' untranslated region.

Numerous aspects and advantages of the invention will be apparent to those skilled in the art upon consideration of the following detailed description which provides illumination of the practice of the invention in its preferred embodiments.

DETAILED DESCRIPTION

The following definitions provide a description of various terms of art discussed in the present invention. As used herein, the term "biological activity" is understood to describe that activity exhibited by the wild type, or naturally occurring, protease, including autocatalytic proteolytic activity. Such activity may be assayed using either natural (i.e. protein) or synthetic substrates. "Cured" refers to the phenomena whereby a plasmid found within a microorganism, introduced by either natural or artificial means, is lost over time and by subsequent cell division, because the selectable marker conferred by that plasmid, such as an auxotrophic marker or resistance to one or more antibiotics, is no longer required for survival, either due to supplemented media or absence of some toxic compound from the media. "Deactivated" Protease X has little to none of the biological activity characteristic of a non-deactivated version of the naturally occurring protease. Deactivation of Protease X may be accomplished by altering the gene encoding the polypeptide. "Extracellular" refers to any or all of the area outside of the cytoplasm of the microorganism. The extracellular area may include, where present, the periplasmic space and/or the surrounding medium.

"Heterologous" refers to proteins, DNA fragments, and/or other materials which do not naturally occur in a particular microorganism. A "heterologous protein product" is one produced by the recombinant expression of a foreign DNA fragment (encoding the particular protein(s) of interest) in a host microorganism which doe not naturally produce that protein. "Host microorganisms" may be procaryotic or eucaryotic cell strains, species, or genera, suitable for introduction and/or expression of heterologous DNA sequences. Examples of suitable procaryotic host microorganisms (also sometimes referred to as bacterial or microbial hosts) include *S. lividans, Bacillus subtilis*, and *Escherichia coli*. Suitable eucaryotic host microorganisms include, for example, yeast, such as *Saccyharomyces cerevisiae*, cultured insect cells, and mammalian cell lines such as COS and CHO. A DNA sequence which has been "optimized" for expression in a particular host microorganism is a DNA sequence containing either or both: (1) codons preferentially utilized by that host; and/or (2) one or more control elements, such as promoters, operators, ribosomal binding sites, and termination sequences used efficiently by that host.

A "processed" protein is initially synthesized as a large precursor polypeptide (the "unprocessed" form), and is subsequently post-translationally modified, such as by cleavage of an amino-terminal signal sequence. Processing can also include cleavage of carboxy-terminal amino acid sequences. A "signal sequence", also referred to as a "leader sequence," "leader peptide," or "signal peptide," is typically composed of the amino-terminal portion of the unprocessed polypeptide, extending from the amino terminal residue to the beginning of the mature protein sequence. The signal sequence is typically a small peptide which directs or targets the entire protein to a particular cellular or extracellular location, or for export from the cell, at which point the signal peptide is cleaved. A "stably transformed" microorganism is one in which some heterologous DNA sequence has been introduced, and that DNA sequence is subsequently maintained and properly segregated upon cell division.

As mentioned previously, *S. lividans* is being used as a prototypical host for the export of heterologous protein products from bacterial hosts. However, *S. lividans* is known to secrete extracellular proteases. These proteolytic activities have been observed to have deleterious effects on such secreted heterologous protein products. Identification, characterization, and elimination of such proteolytic activity may lead to improved quality and yield of secreted heterologous protein products. The present invention describes the isolation and characterization of one such novel proteolytic activity. This proteolytic activity, designated Protease X [SEQ ID NO: 2], is secreted from *S. lividans* into the surrounding culture. The DNA sequence encoding this protein has been cloned and sequenced [SEQ ID NO: 1]. Antibodies have been raised against the polypeptide. Recombinant plasmids, capable of directing the expression of this novel protease in various microorganisms, are also described, as are vectors which enable the translocation of a gene coding for a deactivated Protease X gene into the chromosome of *S. lividans*, thus eliminating the endogenous proteolytic activity characteristic of this gene product.

In order to initially isolate and characterize a protein, sufficient quantities must be obtained. Sufficient quantities of one or more secreted proteases from *S. lividans* may be provided by amplifying exported protease production. Amplification may be accomplished by generating a genomic DNA library in a high copy number vector. A high copy number *S. lividans* plasmid vector capable of directing the expression of secreted proteins in microorganisms may be utilized. The resultant library, containing DNA fragments which may be generated by partial restriction endonuclease digestion of *S. lividans* genomic DNA, when transformed back into *S. lividans*, can lead to increased production of secreted, processed proteases. Clones having elevated levels of proteolytic activity may be identified by assaying transformants for the ability to degrade protein present in an overlay applied to transformed colonies after several hours of growth on selective agar plates. A particularly useful assay employs milk protein, such as casein, in the presence of an antibiotic, like thiostrepton.

Following the isolation of various clones showing elevated levels of secreted proteolytic activity, size comparisons may be made of the inserted genomic DNA fragments present in the plasmids of the various transformants. Those transformants containing plasmids with small genomic DNA inserts but possessing high levels of extracellular proteolytic activity, indicating the existence of a gene encoding a secreted extracellular protease within that particular genomic DNA fragment, can be retained for further analysis.

Increased production of large quantities of a secreted protease may then be obtained by culturing such a S. lividans transformant in rich media until a dense, stationary culture is achieved. It should be noted that the choice of media may affect the molecular weight of the protease obtained. Growth in various medias may result in analogs of the protease differing in amino acid length. Following cultivation, cells are then removed, and the clarified protease-containing culture broth can be subjected to affinity chromotography following dialysis. Those column purified fractions containing proteolytic activity may then be pooled and dialysed further. In a preferred embodiment, this dialysed sample is then lyophilized and resuspended prior to fractionation by gel filtration chromatography. Following the second chromotography procedure, fractions containing proteolytic activity are again pooled. The pooled material may then be dialyzed and lyophilized and then stored at −20° C. or below until further use.

In another embodiment, the clarifed protease-containing culture broth can be treated with protease inhibitors followed immediately by gel filtration chromatography. Aliquots from fractions containing protease activity are then analyzed by SDS-PAGE to identify those fractions containing intact protease, i.e. unhydrolyzed protease. Those fractions containing intact protease may then be dialyzed, lyophilized, and resuspended in a dilute acid buffer. The acid may then be evaporated and the purified, intact protease preparation at −20° C. or below until further use.

Monoclonal and/or polyclonal antibodies may be raised against this column-purified "processed" protease preparation by any one of a number of techniques well known to those skilled in the art. For example, see PCT/US90/05509 for polyclonal antibody production techniques. Issued U.S. Pat. Nos. 4,504,586, 4,558,006, and 4,599,306, hereby incorporated by reference respectively, illustrate monoclonal antibody production. Additionally, antibodies against "unprocessed" Protease X can be raised in similar fashion.

Characterization of the proteolytic activity of Protease X may be conducted by using a synthetic substrate assay, whereby various synthetic peptides are exposed to the protease. Degradation of the substrates is monitored over time by colorimetric measurement. In addition, proteolytic activity under various experimental conditions, such as different temperatures, pH levels, and metal ion concentrations, can be assessed to determine under what conditions the protein retains, or has, optimal activity.

Amino-terminal amino acid sequence analysis of the protease may be attempted using an automated amino acid sequencer. However, both "processed" and "unprocessed" forms of Protease X appear to be resistant to such analysis. As a result, other protein sequencing techniques, such as endoproteolytic digestion, may be used to generate peptide fragments from which amino acid sequence information can then be gathered. Following proteolytic digestion, individual polypeptide fragments suitable for amino acid sequence analysis may be purified by HPLC. After amino acid sequence analysis of the individual HPLC peaks, that tryptic fragment found to contain the least degenerate amino acid sequence (degeneracy based upon the codons coding for those particular amino acids; SEQ ID NO: 5) was used to design a set of oligonucleotides.

This degenerate set of oligonucleotides (encompassing all possible codon combinations for the target amino acid sequence; SEQ ID NO: 6) may then be used to localize the Protease X gene in an S. lividans plasmid directing the expression of the protease. Only genes encoding proteins containing the targeted amino acid sequence will hybridize to the probe set under stringent conditions (temperature near the calculated melting temperature in low salt). Those hybridizing clones can then be subjected to DNA sequence analysis. The DNA sequence then obtained [SEQ ID NO: 1] can be analyzed and the putative coding region for the protein identified [SEQ ID NO: 2]. In addition, other putative open reading frames 5' to the Protease X coding region have been identified. These have been designated ORF 1 and ORF 2, respectively. The putative amino acid sequences for ORF 1 (SEQ ID NO: 3] and ORF 2 [SEQ ID NO:4] are also provided in FIG. 1. The deletion of a 1 kb Pst1 fragment from pHL45 resulted in the loss of 432 bp of vector sequence and 568 bp (from nucleotide position 1 to 568 in FIG. 1) of 5' non-coding DNA from the protease gene. This deletion of DNA upstream of the protease gene led to the loss of Protease X expression.

With the gene encoding Protease X in hand, recombinant plasmids capable of directing the expression of this gene at high levels may be constructed. These constructions, in turn, may enable the production of large quantities of Protease X. This type of high level recombinant expression may be conducted in a variety of host microorganisms, both eucaryotic and procaryotic, employing a variety of expression systems. Construction of such expression systems is readily accomplished by those skilled in the art.

Additionally, specific mutations can be introduced into the Protease X gene of the present invention using site directed mutagenesis. Such mutations may include the deletion, insertion, or substitution of the protease's naturally occurring amino acids. Such mutations may confer altered protein characteristics, which may, for example, improve and/or alter the oxidative, thermal, and/or pH stability of the protein. Mutations of particular relevance may include the elimination of hydrolytically unstable Asn-Gly amino acid sequences, as described in U.S. Pat. No. 4,914,031, which is incorporated herein by reference. Additionally, the ability of Protease X to bind metal ions may be altered by mutagenesis. Modified metal ion binding may improve the protease's catalytic activity or improve its stability under a variety of environmental conditions. See U.S. Pat. No. 4,914,031 for a discussion of the effects of modified metal ion binding.

In addition to genetic manipulations designed to improve or alter the biological activity of Protease X, the gene encoding the protein of the present invention can also be altered to produce a non-active (or much less active, i.e. less than about 5% of the biological activity of the mature protease), in other words, a substantially "deactivated," version of the enzyme. In a preferred embodiment, a substantially deactivated Protease X is produced through the deletion of 305 nucleotides within the coding region of the protease gene, i.e. from nucleotides 1147–1451 as shown in FIG. 1 and SEQ ID NO: 1. This deletion eliminates, or at least greatly reduces, the protease's biological activity. Other deletions or alterations involving greater or lesser numbers of nucleotides from this or other regions of the protein are also envisioned by the present invention.

When a "deactivated" Protease X gene, made in accordance with the present invention, is cloned onto a plasmid capable of directing the integration of DNA into the chromosome of a-microorganism, this construction, when transformed into S. lividans, will, through recombination with the native, biologically active Protease X gene, replace that biologically active protease gene with the "deactivated" gene. A *S. lividans* strain containing a "deactivated" Protease X gene may serve as an improved host for the expression of heterologous proteins.

Also within the scope of the present invention is the construction of an expression system capable of directing the secretion of heterologous proteins in Streptomyces. The secreted heterologous protein may be either the mature, biologically active form of the protein, or it may be in a form which requires additional processing. Such an expression system, harbored in a vector capable of transformation and replication in Streptomyces, may be comprised of a regulatory nucleotide sequence operably associated with the nucleotide sequence encoding the heterologous protein. Because the heterologous protein product is to be secreted into the media, the regulatory sequence will necessarily include a DNA sequence encoding a signal peptide capable of directing the export of the heterologous protein. This requires that the signal peptide be fused to the heterologous polypeptide. In addition, the regulatory sequence will include a promoter sequence capable of directing the transcription of the DNA sequence encoding this fusion protein. One such expression system is disclosed in European Patent Application No. 89113607.9, assigned to Cangene Corp. (Mississauga, Ontario, Canada) and published Jan. 30, 1990. Vectors useful in accordance with the expression system described herein may be maintained extrachromosomally. Alternatively, vectors capable of directing the integration of the expression system plus the heterologous DNA sequence to be expressed into the chromosome of the host may also be utilized in the practice of the present invention.

Various elements of the DNA and amino acid sequences for the Protease X disclosed herein may further be useful in the construction of an expression system for the export of other heterologous protein products from a Streptomyces strain. For example, the promoter for the Protease X gene of the instant invention may be utilized in combination with other elements in a Streptomyces expression and secretion system. Similarly, the Protease X signal peptide may also be combined with other elements in a such a system. Thus, highly efficient expression systems, where either or both the Protease X promoter and the Protease X signal peptide are utilized, will be apparent to those skilled in the art.

For example, expression systems employing the Protease X promoter in combination with signal peptides from other sources may be constructed. What is important is that the signal peptide used in such a system must be capable of directing the export of the heterologous protein to which it is fused. DNA sequences coding for such signal peptides may be derived from other proteins secreted by *S. lividans*, other Streptomyces strains, or from other organisms which secrete protein. The signal sequence may also be synthetic, such as that resulting from a comparison of various signal peptide amino acid sequences, whereby those sequences which are the most conserved are used to construct a so-called consensus signal peptide sequence.

Likewise, the Protease X signal peptide may be employed in a Streptomyces expression system in conjunction with a promoter derived from a DNA sequence for a protein other than Protease X. Such promoters may come from *S. lividans*, other Streptomyces strains, or from other organisms whose promoter sequences are recognized by a Streptomyces RNA polymerase holoenzyme, thus enabling transcription initiation and transcription of the DNA sequences encoding the fusion polypeptide. As with the signal peptide, the promoter sequence may also be synthetic, perhaps reflecting the most conserved nucleotide sequences in various promoters recognized by Streptomyces strains. It is also preferable to select a promoter which is capable of directing high levels of expression, either constitutively or following promoter activation (either by induction or by de-repression), of the fusion protein.

In addition to DNA sequences coding for a promoter and signal peptide, sequences for translational initiation and transcriptional termination are also necessary for a high efficiency expression system. A translational initiation sequence includes a ribosomal binding site, which again can either be a naturally occurring sequence or a synthetic sequence, like a consensus ribosomal binding site for Streptomyces. Similarly, transcription termination signals, such as inverted repeats, may be derived from natural or synthetic sources. Spacing and intervening sequences between the various regulatory elements may also be important. Thus, the expression system may employ spacing and intervening sequences found in DNA sequences encoding naturally occurring proteins expressed in Streptomyces or other bacterial genera, or again consensus spacing and or/intervening sequences may be employed.

In an expression system constructed according to the present invention, the regulatory sequences will be operably linked to the DNA sequence encoding the heterologous protein. The sequence coding for the heterologous protein may be derived from a natural source, or it may be synthetic. A synthetic DNA sequence encoding a heterologous protein may be optimized for expression in Streptomyces. A typical fusion protein construction useful in an expression system such as described herein will find the heterologous protein-encoding DNA sequence linked in-frame with the DNA sequence coding for signal peptide such that upon expression of the fusion protein, the carboxy-terminal amino acid of the signal peptide immediately precedes the amino-terminal amino acid residue of the mature heterologous protein. This fusion protein is then secreted into the media under the direction of the signal peptide, which may or may not be subsequently cleaved.

The Protease X signal peptide may be identified by determining the amino-terminal amino acid sequence of the secreted Protease X and comparing that sequence with the amino acid sequence for the full length Protease X (FIG. 1; SEQ ID NO: 2). Whether or not this signal peptide will be cleaved from a signal peptide/heterologous protein fusion to yield a mature, biologically active form of the protein is unclear. In the event the Protease X signal peptide is not cleaved, it is also possible to insert a small synthetic DNA fragment coding for one or more specific amino acids between the 3' end of the sequence encoding the signal peptide and the 5' end of the DNA sequence encoding the heterologous protein. After expression, secretion, and isolation of the secreted fusion protein, these additional amino acids may allow for cleavage, either by enzymatic or chemical means, of the signal peptide, resulting in a mature form of the desired heterologous protein. Particular amino acid sequences susceptible to various enzymatic or chemical agents are known to those skilled in the art and can readily be incorporated into fusion protein constructs.

The following examples are offered to more fully illustrate the present invention. In addition, the Examples provide preferred embodiments of the present invention but are not meant to limit the scope thereof.

EXAMPLES

Example 1

Isolation of Protease X gene from *S. lividans* Genomic Library

*S. lividans* chromosomal DNA was isolated using a procedure adapted from Saito et al. [(1962) *Biochim. Biophys. Acta.*, vol. 72, pp: 619–29]. A single colony of *S. lividans* TK24 (obtained from D. Hopwood, John Innes Institute) was grown in 200 ml YEME medium [*Genetic Manipulations of Streptomyces*, supra] for 5 days at 30° C. 200 ml of 10% glycerol was added to the culture and the mycelia were collected by centrifugation at 7,000×g for 15 min. The resultant cell pellet was washed twice with 10% glycerol and resuspended in 12 ml lysis buffer (0.15M NaCl, 0.1M EDTA, pH 8.0, 2 mg/ml lysozyme) and incubated with shaking for 30 min. at 37° C.

The mixture was frozen in a dry ice/ethanol bath and thawed slowly with the addition of 35 ml 0.1M Tris-HCl, pH 9.0, 0.1M NaCl, 1% SDS. The mixture was then refrozen in a dry ice/ethanol bath and thawed slowly with the addition of 20 ml phenol (saturated with TE {20 mM Tris-HCl, pH 8.0, 1 mM EDTA}). Proteins were extracted by rocking this mixture at 4° C. for 30 min. The phases were separated by centrifugation and the aqueous phase was then re-extracted with 20 ml phenol/chloroform (1:1). After centrifugation, approximately 35 ml of the aqueous phase was recovered and adjusted to 0.5M by the addition of NaCl. The mixture was then chilled to 4° C. and overlaid with 100 ml of ice-cold ethanol. The chromosomal DNA was recovered by spooling and the isolated DNA resuspended in TE at 4° C.

The DNA was precipitated by adding 0.1 vol acetate EDTA (3M sodium acetate, pH 7.0, 1 mM EDTA) and 0.54 vol isopropanol. The DNA was pelleted by centrifuging the solution at 12,000×g for 15 min. The DNA was resuspended in 5 ml TE. RNAse was added to a final concentration of 50 µg/ml and the solution was incubated at 37° C. for 30 min. The RNAse digested DNA sample was then subjected to phenol extraction. After centrifugation, the aqueous phase was collected and the DNA was precipitated by the addition of 0.1 vol sodium acetate and 2.5 vol ethanol. The resulting suspension was centrifuged at 10,000×g for 15 min. and the pellet resuspended in 6 ml TE. Approximately 5.2 mg of *S. lividans* chromosomal DNA was recovered.

Six aliquots, each containing 50 mg of *S. lividans* genomic DNA, were partially digested with 1.25 units of Sau3A (Boehringer Mannheim Biochemicals) for 10 min. at 37° C. The digestions were stopped by the addition of EDTA to a final concentration of 50 mM. The separate reactions were then pooled. The DNA was extracted with phenol/chloroform and after centrifugation, the aqueous phase was adjusted to 0.3M sodium acetate. The DNA was precipitated by the addition of 2 vol. ethanol. DNA was recovered by centrifugation at 12,000×g for 5 min. The pellet was resuspended in 500 µl TE and then loaded onto a previously prepared 10–40% sucrose gradient. See *Current Protocols in Molecular Biology*, Ausubel et al., Eds., Green Publishing Associates and Wiley-Interscience, 1987. Sucrose gradient ultracentrifugation was conducted at 28,000 rpm for 18 hr. in a Beckman L8-55 ultracentrifuge. 0.5 ml fractions were collected and the DNA precipitated by the addition of 2 vol. ethanol. The DNA was recovered by centrifugation at 12,000×g for 5 min. and the pellets resuspended in 200 µl water. Small aliquots from each fraction were electrophoresed on a 0.8% agarose gel. The DNA was visualized by ethidium bromide staining. Those fractions containing DNA fragments ranging from 4–10 kb in size were used for subsequent cloning experiments.

Appropriately sized Sau3A *S. lividans* chromosomal DNA fragments were ligated into the 5.0 kb BglII fragment from the Streptomyces vector pIJ699 [Kieser et al., (1988) *Gene*, vol. 65, pp:83–91]. The 5.0 kb BglII fragment was prepared by digesting 300 µg of pIJ699 with BglII and EcoRI and then loading the digested DNA onto a 10–40% sucrose gradient, after which ultracentrifugation at 40,000 rpm for 14.5 hr. in a Beckman L8-55 ultracentrifuge was conducted. Fractions were collected, aliquots were analyzed by electrophoresis, and those containing fragments 5.0 kb in size were retained and the DNA precipitated and resuspended as was previously done for the genomic DNA fragments.

0.5 µg of purified BglII digested pIJ699 was ligated to 1.8 µg of 4–10 kb Sau3A partially digested *S. lividans* genomic DNA in 115 µl ligase buffer (*Molecular Cloning*, Maniatis et al., Eds., Cold Spring Harbor Laboratory, 1982) containing 1 unit of T4 DNA ligase (Boehringer Mannheim Biochemicals) for 2 hr. at 23° C. Sodium acetate was added to a final concentration of 0.3M and the DNA was precipitated by the addition of 2 vol. ethanol. The DNA was recovered by centrifugation at 12,000×g for 5 min. and resuspended in 20 µl TE. *S. lividans* protoplasts were transformed with 5 µl of the ligation reaction and plated onto R2YE plates and incubated at 30° C., as described in *Genetic Manipulations of Streptomyces*, supra. After 18 hr., each plate was overlaid with a solution warmed to 55° C. containing 90% skim milk (Difco), 0.4% agar, and 1 mg/ml thiostrepton.

Protease production was assessed by examining the plates for the presence of a "halo" around individual transformants. Of 2,500 transformants screened, 2 produced "halos", designated pHL37 and pHL36. Plasmid DNA from pHL36, which was surrounded by a more profound "halo", was isolated. Restriction analysis of the plasmid revealed that it contained a 9.0 kb insert.

Efforts were then undertaken to determine if a smaller fragment, located within the 9.0 kb piece, could produce "halos" on skim milk plates. The 9.0 kb insert was gel-purified as a HindIII fragment from pHL36. It was subsequently partially digested with 0.00175 units of Sau3A for 10 min. at 37° C. Digestion was stopped by extraction of the sample with phenol/chloroform. DNA was then precipitated from the aqueous phase and the pellet resuspended in 10 µl water. These Sau3A fragments were then ligated to 0.3 µg of the sucrose gradient-purified 5.0 kb BglII fragment of pIJ699 for 1 hr. at room temperature. This ligation mixture was then used to transform *S. lividans* protoplasts as described above. 24 transformants were seen to produce "halos." Plasmid DNA was isolated from "halo"-producing transformants. Restriction analysis showed that the smallest plasmid, designated pHL45, had an insert of 3.4 kb. This 3.4 kb fragment was then cloned as a HindIII fragment into the *E. coli* vector pGEM7ZF(+) (Promega Corp., catalog no. P2251) to yield plasmid pGS4.

Example 2

Purification of Processed Protease X

*S. lividans* cultures harboring pilL45 were grown in 2% dextran, 0.5% HySoy (Sheffield Products, Kraft, Inc., Norwich, N.Y.), 0.25% polypeptone (BBL Microbiology Systems, Lockeysville, Md.), 0.5% $Na_2HPO_4$, 0.1% $MgSO_4$, 0.5% NaCl, 0.3% Yeast Extract (Difco), 34% sucrose, and 0.0005% thiostrepton (Squibb Institute for Medical Research, Princeton, N.J.). After 72 hours of growth at 30° C. the culture was diluted 1:1 with water and then centrifuged at 9,000×g for 45 min. All subsequent procedures in this Example were performed at 4° C. The supernatants were then decanted and dialysed against 10 l of 5 mM MES (2-[N-Morpholino]ethanesulfonic acid, pH 6.4) for 12 hr., with buffer being exchanged 2 times. The resultant dialyzate was then concentrated 10 fold utilizing an Amicon ultrafiltration stirred cell device equipped with a YM-10 membrane. After concentration, the solution was diluted 1:1 with 5 mM MES, pH 6.4, and applied to a 350 ml CM-Sepharose column equilibrated in the same buffer. A flow rate of 4 ml/min. was used.

After washing the column with buffer, the dialysed protein sample was loaded onto the column. The protein was eluted using a linear gradient of 0.0 to 0.5M NaCl. The eluate's $A_{280}$ was monitored and 8 ml fractions were collected. Fractions found to contain protein were assayed using the azocasein method, where 100 µl aliquots of the fractions are mixed with 900 µl of 0.6% azocasein in 20 mM Tris pH 8.0 and incubated at 37° C. for 1 hr. Following the incubation, the assay reaction was terminated by the addition of 200 µl of 10% trichloroacetic acid and incubation at room temperature for several minutes. The solutions were then neutralized by adding 200 µl 0.2N NaOH to each sample. Samples were centrifuged 2 min. The supernatants were removed and the activity of the fractions was determined from the increase in absorbance at 420 nm.

Fractions 65–90 were found to contain the activity peak and were thus pooled. The pooled fractions were then dialysed against 5 liters of 5 mM MES, pH 6.4, for 12 hr. at 4° C. After dialysis, the sample was lyophilized. The lyophilized powder was then dissolved in 0.5 ml 10 mM MES, 150 mM NaCl, pH 6.4, and further purified by gel filtration chromatography on a Pharmacia Superose System 12 column, using the FPLC system. The column was developed using a flow rate of 0.5 ml/min., and 0.5 ml fractions were collected. Fractions containing protein as indicated by the $A_{280}$ were again assayed for proteolytic activity, and also analyzed on a SDS-PAGE gel. The fractions containing proteolytic activity were dialysed against 5 mM MES, pH 6.4, lyophilized and stored at −20° C. Those fractions containing proteolytic activity were homogeneous by SDS-PAGE, but the apparent molecular weight (17,000 D; 17 kD) was smaller than the initial starting material (22,000 D; 22 kD). This shift in molecular size was attributed to proteolytic cleavage of the protease during the purification procedure.

Example 3

Protease Purification

Conditions were optimized to prevent autodigestion of the protease. 150 ml cultures were harvested earlier in the growth cycle (at 36 hr.), diluted 1:1 with $H_2O$ and centrifuged. The supernatants were recovered and adjusted to 2.5 mM EDTA, 1 mM PMSF and immediately subjected to gel filtration chromatography. 10 ml of the supernatant was applied to a 200 ml Sephacryl S-300 column equilibrated in 20 mM MES, 100 mM NaCl, 2.5 mM EDTA, 1 mM PMSF, pH 6.5. The column was developed with a flow rate of 1 ml/min. The absorbance of the eluate was monitored at 280 nm and 2 ml fractions were collected. After samples had been collected for the initial 10 ml loading, an additional 10 ml of similarly treated supernatant was loaded onto the column and fractions were collected as before. Fractions containing protein were analyzed by SDS-PAGE, and those fractions found to contain intact protease (Fractions 85–115) were pooled and lyophilized. The powder was redissolved in 0.1% trifluoroacetic (TFA) acid and diafiltered against 0.1% TFA to remove salt. The TFA was then evaporated and the pure protein was stored as a powder at −20° C. until further use.

Example 4

Proteolytic Activity

The characteristics of the protease reaction catalyzed by this enzyme were determined using the synthetic substrate assay where various synthetic substrates are dissolved at a concentration of 100 mg/ml in dimethylsulfoxide (DMSO). 200 µl aliquots from bacterial culture supernatants were mixed with 780 µl of 5 mM Tris, 25 mM NaCl, pH 7, and incubated at the desired temperature Digestions were then initiated by the addition of 20 µl of substrate and the rate of absorbance at 405 nm was followed for several minutes.

Here, the broth from recombinant *S. lividans* containing pHL45, as well as the broth from an identical *S. lividans* culture containing a control plasmid only (pIJ699), were compared for proteolytic activity by directly assaying activity in the presence of several different substrates. This experiment was conducted at 37° C. pH 7.0 and 65° C. pH 7 5, in the presence of 10 mM calcium. The substrates tested were: succinyl-ala-ala-pro-phe-pNitroanilide, succinyl-tyr-leu-val-pNitroanilide, ala-pNitroanilide, and leu-pNitroanilide. The only substrate upon which the protease showed activity above that of the control was succinyl-ala-ala-pro-phe-pNitroanilide, a substrate also utilized for chymotrypsin, subtilisin, and cathepsin G. In addition, fragments generated during peptide mapping of the protease indicate that the protease preferentially processes proteins aminoterminally of tyrosine. The temperature optimum for the proteolytic reaction was determined using succinyl-ala-ala-pro-phe-pNitroanilide in 10 mM Tris, 25 mM NaCl, pH 7.0. The results are shown in Table 1.

TABLE 1

| Sample | Temperature | Activity (dA/min)[a] |
|---|---|---|
| 1 | 30.000 | 0.008 |
| 2 | 40.000 | 0.017 |
| 3 | 50.000 | 0.042 |
| 4 | 60.000 | 0.074 |
| 5 | 65.000 | 0.085 |
| 6 | 70.000 | 0.047 |

[a]The activity listed is that obtained by subtracting the activity of the control broth from that of the broth containing protease, measured under the same conditions.

The protein's activity appears to increase until it is no longer thermally stable Even at 70° C. the initial catalytic rate is very fast, as indicated by the initial large increase in absorbance. However, the activity drops off dramatically as the enzyme apparently becomes denatured. The temperature optimum for the cleavage of succinyl-ala-ala-pro-phe-pNitroanilide is 65° C. where the catalytic rate remains linear for at least 2 min. In the azocasein assay, where longer incubation times are used, the temperature optimum was found to be 60° C. The pH optimum for the 65° C. reaction was also tested. The pH optimum was found to be pH 7.5. These results appear in Table 2.

TABLE 2

| Sample | pH | Activity (dA/min)[a] |
|---|---|---|
| 1 | 6.000 | 0.048 |
| 2 | 7.000 | 0.085 |
| 3 | 7.500 | 0.190 |
| 4 | 8.000 | 0.105 |

[a]The activity listed is that obtained by subtracting the activity of the control broth from that of the broth containing protease, measured under the same conditions.

The addition of additives to the reaction was also tested and is shown in Table 3.

TABLE 3

| Sample | Additive | Activity (dA/min)[a] |
| --- | --- | --- |
| 1 | — | 0.170 |
| 2 | 5 mM EDTA | 0.120 |
| 3 | 5 mM CaCl$_2$ | 0.235 |
| 4 | 20 mM CaCl$_2$ | 0.251 |
| 5 | 20 mM MgCl$_2$ | 0.250 |
| 6 | 1 mM PMSF | 0.000 |

[a]The assays were performed for 2 min. at 65° C. at pH 7.5. Activity listed is that obtained by subtracting the activity of the control broth from that of the broth containing protease, measured under the same conditions. The reaction was found to be totally inhibited by the addition of PMSF, a serine protease inhibitor. In addition, the protease's activity was enhanced by the addition of calcium to 20 mM. Further, 20 mM magnesium also appears to enhance the protease's ac tivity.

Example 5

Amino Acid Sequence of Tryptic Fragment from Protease X

Amino-terminal sequence analysis of both the intact (22 kD) and "processed" (17 kD) form of the protease revealed that the amino-terminal residue is blocked in both species, suggesting they share the same amino-terminus and that any post-translational amino acid processing may occur at the carboxy-terminus. Additionally, because the amino-terminus is blocked, traditional amino-terminal amino acid sequencing of this protease was not possible. Thus, tryptic digestion of the molecule was conducted.

The amino acid sequence of a tryptic fragment of the purified "processed" protease was identified to confirm the cloning of the gene encoding Protease X. The 17 kD "processed" Protease X was digested with sequenal grade trypsin (Boehringer Mannheim Biochemicals, catalog no. 1047 841) for 18 hrs. at 37° C. The peptides generated were separated on a Vydac C4 HPLC column previously equilibrated in 0.1% TFA in water. Peptide fragments were eluted using a linear gradient of up to 68% acetonitrile in the same buffer using a flow rate of 0.75 ml/min. Fractions with high absorbances at 280 nm were dried and run on an Applied Biosystems 477 protein sequencer. The sequence of one fraction was determined to be [SEQ ID NO: 5]:
POSITION:

1-2-3-4-5-6-7-8-9-10-11-12-13-14-15-16-17-18-19

AMINO ACID:

L-A-E-S-S-S-G-A-D--F--A--Y--Y-E--G--N--D--S--R

Table 4 provides three-letter and one-letter codes for each of the 20 amino acids found in naturally occuring proteins.

TABLE 4

| Amino acid | Three-letter Abbreviation | One-letter Abbreviation |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Example 6

Synthesis of Probe for Detection of Protease X Gene

Streptomyces DNA is known have a genomic nucleotide base composition of 73% G+C [Enquist et al., (1971) Dev. Ind. Microbiol., vol 12, pp: 225–36]. The high G+C content of the Streptomyces genome is reflected in a strong bias toward the use of codons that have either a G or C in the third position [Bibb et al., (1984) Gene, vol. 30, pp: 157–66]. In view of these factors, a synthetic oligonucleotide was designed based upon the amino acid sequence determined in Example 5. The sequence of the mixed 33-mer oligonucleotide probe corresponds to amino acid positions 7–17 in the above tryptic fragment and is as follows [SEQ ID NO: 6]:

5'-GG(G/C) GC(G/C) GAT TTC GC(G/C) TAC TAC GAG GG(G/C) AAC GAC-3'

Please note that in SEQ ID NO: 6, G/C is represented by S. This probe was synthesized using the phosphotriester method of Beaucage et al. [(1981) Tetrahedron Letters, vol. 22, pp: 1859–62].

Example 7

Protease X Gene Characterization

The 3.4 kb insert from pGS4 was mapped with restriction enzymes MluI, SphI, PstI, XhoI, SacI, ClaI, EcoRV, and BglII. To localize the Protease X gene within this insert, pGS4 was digested with MluI or XhoI and the resultant fragments were resolved by agarose gel electrophoresis. The restriction fragments were then transferred to GeneScreen Plus (DuPont). After blotting, the membrane was then prehybridized in 5×Denhardt's solution containing 1% SDS, 5×SSPE (Molecular Cloning, supra), and 100 µg/ml heat-treated salmon sperm DNA at 65° C. for 2 hrs. The prehybridization solution was then discarded. The membrane was then hybridized in 1×Denhardt's solution with 1% SDS, 5×SSPE, 100 µg/ml heat-treated salmon sperm DNA, and $10^7$ cpm (1 pmol) of the oligonucleotide from Example 6 [SEQ ID NO: 6] labelled with $^{32}$p. Hybridization was allowed to proceed at 65° C. for 3 hrs. The membrane was then washed twice for 5 min. at room temperature with 6×SSC (Molecular Cloning, supra) containing 0.1% SDS. After washing, the membrane was autoradiographed. The developed X-ray film revealed that a 1.5 kb MluI fragment and a 2.5 kb XhoI fragment hybridized to the probe. Thus, a 0.6 kb fragment (located 0.9 kb–1.5 kb from the 5' end of the insert) that was shared by both hybridizing fragments contained a portion of the coding region for Protease X.

The 3.4 kb insert in pGS4 was then sequenced, beginning at the 5' end using the SP6 primer (Promega Corp. catalog no. Q5011). After obtaining some partial sequence, new complementary primers corresponding to more distal sequences were synthesized and used to sequence 1910 bp of DNA beginning at the 5' end of the 3.4 kb pGS4 insert (FIG. 1; SEQ ID NO: 1).

An open reading frame (ORF) containing sequences coding for the amino acids comprising the tryptic fragment from Example 3 was found between nucleotides 1147 and 1827. The DNA encoding those specific amino acids identified in the tryptic fragment in Example 3 corresponds to nucleotides 1483–1539. The Protease X ORF has the characteristics of a typical Streptomyces protein in that 96% of the codons have G or C in the third position. In addition, upstream of the presumed ATG initiation codon, there is a putative ribosomal binding site (FIG. 1), showing complementarity to the 3' end of the 16S ribosomal RNA of *S. lividans* [Bibb et al., (1982) *Mol. Gen. Genet.*, vol. 187, pp: 265–277]. The sequence following the initiation codon encodes amino acids characteristic of a typical signal peptide in that there is a basic N-terminal region (Arg at amino acid position 2) followed by a hydrophobic region between amino acids 10 to 32 (FIG. 1).

The ORF for Protease X codes for 227 amino acids [SEQ ID NO: 2], although it is presumed that signal peptide processing would shorten the length of the mature protease. A perfect 16 bp inverted repeat (FIG. 1) was found downstream of the TGA stop codon.

Example 8

Deletion in the Protease X Gene

To engineer a deletion in the Protease X gene, a plasmid, pLBS18, was constructed containing unique BglII and ClaI sites within the gene coding for this polypeptide. pLBS18 was generated in the following manner: Plasmids pUC19 (BRL catalog no. 5364SA) and pGS4 were both digested with HindIII and then subjected to electrophoresis through a 0.8% low-melting point agarose gel (FMC Bioproducts, catalog no. 50101). The 3.4 kb HindIII fragment from pGS4 and the HindIII-linearized pUC19 were eluted from the gel following the GeneScreen protocol (Bio 101, Inc., catalog no. 3105). 1 µg of each gel-purified fragment was then ligated in a 10 µl reaction (conditions specified by BRL). The resultant ligation products were used to transform *E. coli* strain JM109 by electroporation [Dower et al., (1988) *Nucleic Acids Research*, vol. 16, pp: 6127–45]. Transformants were selected by plating on LB plates containing 100 µg/ml Ampicillin. Plasmid DNA was isolated from ampicillin resistant colonies by standard techniques [*Molecular Cloning*, supra] and subjected to restriction analysis to identify those transformants harboring plasmids containing the 3.4 kb HindIII insert from pGS4. Those clones found to contain the insert were designated pLBS18.

To generate a Protease X gene containing a BglII/ClaI deletion, pLBS18 was digested with BglII and ClaI, excising a 0.3 kb fragment from the coding region of the protease gene. The "sticky" ends of the digested DNA were then filled using the Klenow fragment of *E. coli* DNA polymerase I (Boehringer Mannheim Biochemicals, catalog no. 997455) according to procedures described in *Molecular Cloning*, supra. Following the end-filling reaction, the sample was extracted with phenol/chloroform (1:1) and the DNA precipitated from the aqueous phase with ethanol. 1 µg of this end-filled DNA was then ligated in a 25 µl reaction. After ligation, the mixture was used to transform *E. coli* JM109 by electroporation. Following plating of the transformation mixture on LB plates containing 100 µg/ml ampicillin, plasmid DNA was isolated from ampicillin resistant colonies by standard techniques. Restriction analysis of plasmid DNA from these transformants identified a clone containing a 0.3 kb deletion between the BglII and ClaI sites in the Protease X gene. This clone was designated pLBS19.

Example 9

Integration Vector Construction

To substitute the deleted Protease X gene generated in Example 8 for the wild type Protease X gene in the *S. lividans* chromosome, an integration vector, designated pLBS27, was constructed as follows: Plasmid pLBS19 was digested with BamHI and KpnI, followed by phenol/chloroform extraction. The doubly digested DNA was precipitated with ethanol and resuspended in water. Plasmid pIJ699 was digested with BamHI and KpnI and then electrophoresed on a 0.8% low-melting point agarose gel. The 3.3 kb pIJ699 fragment was eluted from the gel with GeneClean (Bio 101, Inc., catalog no. 3105) in accordance with established procedures. 1 µg of BamHI/KpnI digested pLBS19 was ligated to 1 µg of the gel-purified BamHI/KpnI 3.3 kb fragment from pIJ699 in a 10 µl reaction. The ligation products were then transformed in *E. coli* JM109 by electroporation. Following transformation and selection on LB plates containing 100 µg/ml ampicillin, plasmid DNA was isolated from the ampicillin-resistant transformants. Restriction analysis of the resultant plasmid DNA was used to identify desired clones, one of which was designated pLBS27. pLBS27 has an *E. coli* origin of replication, does not have a Streptomyces origin of replication, contains selectable markers for growth in *E. coli* (ampicillin and viomycin resistance) or Streptomyces (viomycin), and has an engineered Protease X deletion mutation.

Example 10

Integration of Protease X Deletion into *S. lividans*

26 µg of pLBS27 was transformed into *S. lividans* TK24 by standard techniques described in *Genetic Manipulation of Streptomyces*, supra, except that the transformation mixture was plated onto R2YE plates containing 50 µg/ml viomycin (Sigma, catalog no. V4627). Viomycin resistant colonies were selected and grown up in Tryptic Soy Broth (TSB, Difco, catalog no. 0370-02-0) containing 8 µg/ml viomycin.

Attempts to isolate plasmid DNA from viomycin resistant cultures proved unsuccessful, suggesting chromosomal integration had occurred. Two viomycin resistant colonies were saved and designated HL255 and HL256. HL256 was then grown to saturation in TSB +8 µg/ml viomycin. The culture was then streaked on non-selective R2YE media and allowed to sporulate. Spores were then harvested and streaked onto another R2YE plate and allowed to sporulate a second time. These spores were then harvested, diluted, and spread onto R2YE plates. Individual colonies were picked and tested for viomycin sensitivity by replica plating onto R2YE only plates and R2YE+viomycin plates. One viomycin sensitive colony, designated HL257, was subsequently retained. PCR technology was used to verify that this strain had a deletion spanning nucleotides 1147–1451 [SEQ ID NO: 1] in the sequence as shown in FIG. 1.

Therefore, HL257 has a gene with the Protease X gene deletion substituted for the wild type protease gene. HL257 is Protease X deficient and should serve as a more suitable host for the production of secreted heterologous protein products.

While the present invention has been described in terms of preferred embodiments, it is understood that variations and modifications will occur to those skilled in the art in light of the above description. Therefore, it is intended that the appended claims cover all such variations which come within the scope of the invention as claimed.

What is claimed is:

1. A purified and isolated DNA molecule consisting of a nucleic acid sequence that encodes the protease polypeptide of SEQ ID NO:2.

2. A purified and isolated DNA molecule consisting of nucleotides 1452–1827 of SEQ ID NO:1.

3. A purified and isolated DNA molecule consisting of nucleotides 1147–1827 of SEQ ID NO:1.

4. A plasmid comprising the DNA molecule of claim 1 operably linked to an expression control element that effects the expression of the DNA of claim 1.

5. A plasmid comprising the DNA molecule of claim 3 operably linked to an expression control element that effects the expression of the DNA of claim 3.

6. A cultured host cell transformed with the plasmid of claims 4 or 5.

* * * * *

UNITED STATES PATENT AND TRADEMARK OFFICE
CERTIFICATE OF CORRECTION

PATENT NO.   : 5,516,685
DATED        : May 14, 1996
INVENTOR(S)  : Henri Lichenstein It is certified that error appears in the above-identified patent and that said Letters Patent is hereby corrected as shown below:

Column 10, line 55, "piIL45" should be --pHL45--.

Signed and Sealed this

Sixth Day of August, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 2261 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| AAGCTTCTAG | AGATCCCGCC | CCCTTCCAGC | CACTCCCGGT | ACGCGGTGGA | CTGGCGGGCG | 60 |
| GCCTCCCAGT | ACGCGTCCTC | CAGGGCGGGG | AAGACCGCGT | CCAGCTCGGC | CCGGGTGCGG | 120 |
| GCGGCCAGCA | GCAGGCGTAC | GCCGAGGGGG | TCGCCGTACA | GGCGCCGCAC | CGCCGTGTCG | 180 |
| GGGCGGGACT | GGGAACTGGG | CTGGCAGACC | GTGACGACCT | CGCCGGTGGC | GACCAGGGAG | 240 |
| GCGGCCGTGT | GGTAGTCGCC | GTGCAGCACC | CGGGGGTTGA | GGCCGACGGC | GCGCAGCATG | 300 |
| CGGTGCACGC | CGTCCCATTC | GCCGTCGACG | GTGGGGTCGA | CCATCCACCG | GTCGTCGGCG | 360 |
| AGGTCGGCGA | GGCGGACGAC | GGGCCGGGCG | GCCGCGGGGT | GGTCGGCGGG | CAGCATGACG | 420 |
| AACTGCGGTT | CGCGCTCGAC | CAGGACGCGC | AGCCGCAGGT | CCTCGGGGAT | GTGCAGCGCA | 480 |
| CAGCCCTCGA | CCTCGTGCAC | GAAGGCGACG | TCGAGCTGAC | CGTCGGTCAC | CCGGCGCAGC | 540 |
| AGCGCGTTGG | CGGAGACGTC | CATCTGCAGG | GTCGGTTCCA | GGCCCGGCCG | TCTGAGCCGG | 600 |
| CGCAGCCAGC | CGGCCAGGGC | CCGGCTGGCC | GTGGAGCCGA | CCCGCAGCCT | GCTGTCGCCG | 660 |
| CCGGCCGCGG | CGGCGCGGGC | CTCGCGGACC | AGGGTGTTCA | TGTCGGTCAG | CAGCGGACGG | 720 |
| GCCCGGCCGA | GCACCGTCCG | GCCGAGCGGG | GTGGGGCGGC | AGCCGGTGCG | CTCCCGGGTG | 780 |
| AACAGCGGTC | CGCCCAGGGC | CTGTTCGATG | CGGGTCAACT | GAGTGCTCAA | CGTGGGCTGT | 840 |
| GCGACACCCA | GTCGGCGTGC | CGCCCGGTGC | AGGCTGCCGG | CGTCGGCGAT | GGCGCACAGT | 900 |
| GCGCGTAGGT | GCCTCACCTC | GAGCTCCATG | CAGGGAGCGT | AAAGCGGAAC | AGTTGGTTGC | 960 |
| GCCAGGTGAA | CAAAACGCGG | CGGATCAGGG | CGAGTTCTGC | ACTCTGGTCA | AAGCTGGAAC | 1020 |
| GAGAGTGGCC | GGGCGGTGGG | TGATAGCCCG | GCCCTATCAC | CTGTTGCCAT | CATCACAGCG | 1080 |
| GGCTCATGGG | CGCCCCACAC | TCACCGGTGA | CGACTTCTCC | CCACTCCCCC | ACTCAAGGAG | 1140 |
| TCATCGATGC | GTATCACCCT | GCCCCTTCTT | TCCACCGCGG | TCGGTCTCGG | CCTGACGGCC | 1200 |
| GCCGTGCTCG | GCACCGGCCC | CGCCGCGACG | GCCGCGGCGC | CCAGGAGCC | GGTCAGAGCC | 1260 |
| GCCCAGCTCG | GCTACCAGCC | CTCGGCCGGC | TCGGGCGAGG | ACGCGGCCGC | CAACCGCGCG | 1320 |
| TTCTTCGAGG | CGGTCGTCAA | GTCCGTCGCC | GAGAAGCGCG | CCGCCAACCC | GTCCGCCGCC | 1380 |
| GCGGCCGTCA | CCGTCTACTA | CAGCGCCACC | AACGCGCCGA | GCTTCCGTTC | CCAGATATCC | 1440 |
| CGCTCCGCCC | AGATCTGGAA | CAGCTCGGTG | TCCAACGTAC | GGCTCGCGGA | GTCGAGTTCC | 1500 |
| GGCGCGGACT | TCGCGTACTA | CGAGGGCAAC | GACTCGCGCG | GCTCGTACGC | GTCCACGGAC | 1560 |
| GGGCACGGCA | GCGGCTACAT | CTTCCTCGAC | TACCGCCAGA | ACCAGCAGTA | CGACTCGACC | 1620 |
| CGCGTGACCG | CCCACGAGAC | CGGGCACGTG | CTCGGCCTGC | CCGACCACTA | CTCCGGGCCG | 1680 |
| TGCAGCGAGC | TGATGTCGGG | CGGCGGCCCC | GGCCCGTCCT | GCACCAACCC | CTACCCGAAC | 1740 |
| TCCACCGAGC | GCAGCCGGGT | GAACCAGCTG | TGGGCCTACG | GCTTCCAGGC | CGCCCTCGAC | 1800 |

```
AAGGCGCTGG AGAAGGCCTC CCAGCGCTGA CGTACGCGGA CCACCGTGCG GGCGGCCCGG    1860

CCGGGCCGCC CGCACGCGTG CGCGCTCCCT CCACCTCCGC TTGGGCAACC TAGTTAAAGG    1920

TAAAAAGTGA AAATAAAAAA GGAAGAAAAG GTGAAGGGAA AAAAAAAGAA GAAAAAAGA     1980

GAAAAAAAAA AAAAATATTA ATAAAGGAG  AAGTAAAAAG AAGGAAAAAT TGGAAAGGTA    2040

ATAGGGTATA GGAGGTATAG ATAAGTGAGA TGCGTGGGGC TATATGAGAG AAGTAATGGA    2100

AAAAAGAAG  AGTAGCTTAG TAGAAAGAAA GAGTTGAGAA AAAAGTAAGT TACGAGTAGT    2160

AGAGAGGTCA AGTCTAATTA GAGAAAGTAA GGAGAGGAAG AGAAGAGAAC TAGAAAAGGA    2220

AAAATTGGAA AGGGCGATT  TCGCTACTAC GAGGGAACGA C                        2261
```

( 2 ) INFORMATION FOR SEQ ID NO:2:

( i ) SEQUENCE CHARACTERISTICS:
    ( A ) LENGTH: 227 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..226

( x i ) SEQUENCE DESCRIPTION: SEQ ID NO:2:

```
Met Arg Ile Thr Leu Pro Leu Leu Ser Thr Ala Val Gly Leu Gly Leu
 1               5                  10                      15

Thr Ala Ala Val Leu Gly Thr Gly Pro Ala Ala Thr Ala Ala Ala Pro
                 20                 25                  30

Gln Glu Pro Val Arg Ala Ala Gln Leu Gly Tyr Gln Pro Ser Ala Gly
                 35                 40                  45

Ser Gly Glu Asp Ala Ala Ala Asn Arg Ala Phe Phe Glu Ala Val Val
             50                 55                  60

Lys Ser Val Ala Glu Lys Arg Ala Ala Asn Pro Ser Ala Ala Ala Ala
 65                     70                  75

Val Thr Val Tyr Tyr Ser Ala Thr Asn Ala Pro Ser Phe Arg Ser Gln
 80                 85                  90                      95

Ile Ser Arg Ser Ala Gln Ile Trp Asn Ser Ser Val Ser Asn Val Arg
                100                105                 110

Leu Ala Glu Ser Ser Ser Gly Ala Asp Phe Ala Tyr Tyr Glu Gly Asn
                115                120                 125

Asp Ser Arg Gly Ser Tyr Ala Ser Thr Asp Gly His Gly Ser Gly Tyr
            130                135                 140

Ile Phe Leu Asp Tyr Arg Gln Asn Gln Gln Tyr Asp Ser Thr Arg Val
    145                150                 155

Thr Ala His Glu Thr Gly His Val Leu Gly Leu Pro Asp His Tyr Ser
160                 165                 170                 175

Gly Pro Cys Ser Glu Leu Met Ser Gly Gly Pro Gly Pro Ser Cys
                180                185                 190

Thr Asn Pro Tyr Pro Asn Ser Thr Glu Arg Ser Arg Val Asn Gln Leu
            195                200                 205

Trp Ala Tyr Gly Phe Gln Ala Ala Leu Asp Lys Ala Leu Glu Lys Ala
            210                215                 220

Ser Gln Arg
            225
```

( 2 ) INFORMATION FOR SEQ ID NO:3:

( i ) SEQUENCE CHARACTERISTICS:
 ( A ) LENGTH: 73 amino acids
 ( B ) TYPE: amino acid
 ( C ) STRANDEDNESS: single
 ( D ) TOPOLOGY: linear ( i i ) MOLECULE TYPE: protein ( i x ) FEATURE:
 ( A ) NAME/KEY: Protein
 ( B ) LOCATION: 1..72

( x i ) SEQUENCE DESCRIPTION: SEQ ID NO:3:

```
Met Arg Cys Thr Pro Ser His Ser Pro Ser Thr Val Gly Ser Thr Ile
 1               5                  10                  15

His Arg Ser Ser Ala Arg Ser Ala Arg Arg Thr Thr Gly Arg Ala Ala
            20                  25                  30

Ala Gly Trp Ser Ala Gly Ser Met Thr Asn Cys Gly Ser Arg Ser Thr
            35                  40                  45

Arg Thr Arg Ser Arg Arg Ser Ser Gly Met Cys Ser Ala Gln Pro Ser
            50                  55                  60

Thr Ser Cys Thr Lys Ala Thr Ser Ser
     65                  70
```

( 2 ) INFORMATION FOR SEQ ID NO:4:

( i ) SEQUENCE CHARACTERISTICS:
 ( A ) LENGTH: 40 amino acids
 ( B ) TYPE: amino acid
 ( C ) STRANDEDNESS: single
 ( D ) TOPOLOGY: linear ( i i ) MOLECULE TYPE: protein ( i x ) FEATURE:
 ( A ) NAME/KEY: Protein
 ( B ) LOCATION: 1..39

( x i ) SEQUENCE DESCRIPTION: SEQ ID NO:4:

```
Met Ser Val Ser Ser Gly Arg Ala Arg Pro Ser Thr Val Arg Pro Ser
 1               5                  10                  15

Gly Val Gly Arg Gln Pro Val Arg Ser Arg Val Asn Ser Gly Pro Pro
            20                  25                  30

Arg Ala Cys Ser Met Arg Val Asn
            35
```

( 2 ) INFORMATION FOR SEQ ID NO:5:

( i ) SEQUENCE CHARACTERISTICS:
 ( A ) LENGTH: 19 amino acids
 ( B ) TYPE: amino acid
 ( C ) STRANDEDNESS: single
 ( D ) TOPOLOGY: linear ( i i ) MOLECULE TYPE: protein ( x i ) SEQUENCE DESCRIPTION: SEQ ID NO:5:

```
Leu Ala Glu Ser Ser Ser Gly Ala Asp Phe Ala Tyr Tyr Glu Gly Asn
 1               5                  10                  15

Asp Ser Arg
```

( 2 ) INFORMATION FOR SEQ ID NO:6:

( i ) SEQUENCE CHARACTERISTICS:
 ( A ) LENGTH: 29 base pairs
 ( B ) TYPE: nucleic acid

```
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGGCGATTTC  GCTACTACGA  GGGAACGAC                                          29

( 2 ) INFORMATION FOR SEQ ID NO:7:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: linear ( i i ) MOLECULE TYPE: protein ( x i ) SEQUENCE DESCRIPTION: SEQ ID NO:7:

Gly  Ala  Asp  Phe  Ala  Tyr  Tyr  Glu  Gly  Asn  Asp
     1                  5                        10
```